(12) United States Patent
Johnson et al.

(10) Patent No.: US 8,849,403 B2
(45) Date of Patent: Sep. 30, 2014

(54) ACTIVE IMPLANTABLE MEDICAL SYSTEM HAVING EMI SHIELDED LEAD

(75) Inventors: Robert Shawn Johnson, North Tonawanda, NY (US); Robert A. Stevenson, Canyon Country, CA (US); Warren S. Dabney, Orchard Park, NY (US); Holly Noelle Moschiano, Lancaster, NY (US); Kishore Kumar Kondabatni, Williamsville, NY (US); Neal Nesselbeck, Lockport, NY (US); Joseph Spaulding, Williamsville, NY (US); Henry R. Halperin, Pikesville, MD (US); Albert C. Lardo, Baltimore, MD (US)

(73) Assignee: Greatbatch Ltd., Clarence, NY (US)

( * ) Notice: Subject to any disclaimer, the term of this patent is extended or adjusted under 35 U.S.C. 154(b) by 348 days.

(21) Appl. No.: 12/788,123

(22) Filed: May 26, 2010

(65) Prior Publication Data
US 2010/0280584 A1 Nov. 4, 2010

Related U.S. Application Data

(63) Continuation-in-part of application No. 12/686,137, filed on Jan. 12, 2010, which is a continuation-in-part of application No. 12/489,921, filed on Jun. 23, 2009, now Pat. No. 7,751,903, said application No. 12/489,921 is a continuation-in-part of application No. 10/123,534, filed on Apr. 15, 2002, now Pat. No. 7,844,319.

(60) Provisional application No. 61/149,833, filed on Feb. 4, 2009, provisional application No. 61/144,102, filed on Jan. 12, 2009, provisional application No. 60/283,725, filed on Apr. 13, 2001.

(51) Int. Cl.
| *A61N 1/372* | (2006.01) |
| *A61B 5/00* | (2006.01) |
| *A61N 1/05* | (2006.01) |
| *G01R 33/28* | (2006.01) |
| *A61N 1/37* | (2006.01) |
| *A61B 18/00* | (2006.01) |
| *A61B 5/055* | (2006.01) |
| *A61B 5/042* | (2006.01) |
| *A61B 19/00* | (2006.01) |
| *A61N 1/08* | (2006.01) |

(52) U.S. Cl.
CPC .............. *G01R 33/285* (2013.01); *A61N 1/3718* (2013.01); *A61B 5/415* (2013.01); *A61B 2018/00839* (2013.01); *A61B 5/055* (2013.01); *A61B 5/042* (2013.01); *A61B 5/7203* (2013.01); *A61B 2019/5236* (2013.01); *A61N 1/05* (2013.01); *A61B 5/418* (2013.01); *A61N 2001/086* (2013.01)
USPC ................................. 607/36; 607/37; 607/116

(58) Field of Classification Search
USPC ................................ 607/36–37, 116; 333/182
See application file for complete search history.

(56) References Cited

U.S. PATENT DOCUMENTS

| 7,038,900 | B2 | 5/2006 | Stevenson et al. |
| 2005/0007718 | A1 * | 1/2005 | Stevenson et al. ............ 361/118 |
| 2005/0113876 | A1 * | 5/2005 | Weiner et al. .................... 607/36 |
| 2007/0043399 | A1 * | 2/2007 | Stevenson et al. ............. 607/37 |
| 2008/0024912 | A1 | 1/2008 | Mallary et al. |
| 2010/0023000 | A1 | 1/2010 | Stevenson et al. |
| 2010/0160997 | A1 | 6/2010 | Johnson et al. |
| 2011/0118813 | A1 * | 5/2011 | Yang et al. ..................... 607/116 |

* cited by examiner

*Primary Examiner* — Joseph Stoklosa
(74) *Attorney, Agent, or Firm* — Michael F. Scalise

(57) ABSTRACT

A lead extending exteriorly from an active implantable medical device (AIMD) is at least partially ensheathed within an electromagnetic interference (EMI) shield. The AIMD has a conductive equipotential surface to which the EMI shield may be conductively coupled. An impeding circuit may be provided for raising the high frequency impedance of the lead. An energy diversion circuit may also be provided for conductively coupling the lead to the EMI shield.

37 Claims, 13 Drawing Sheets

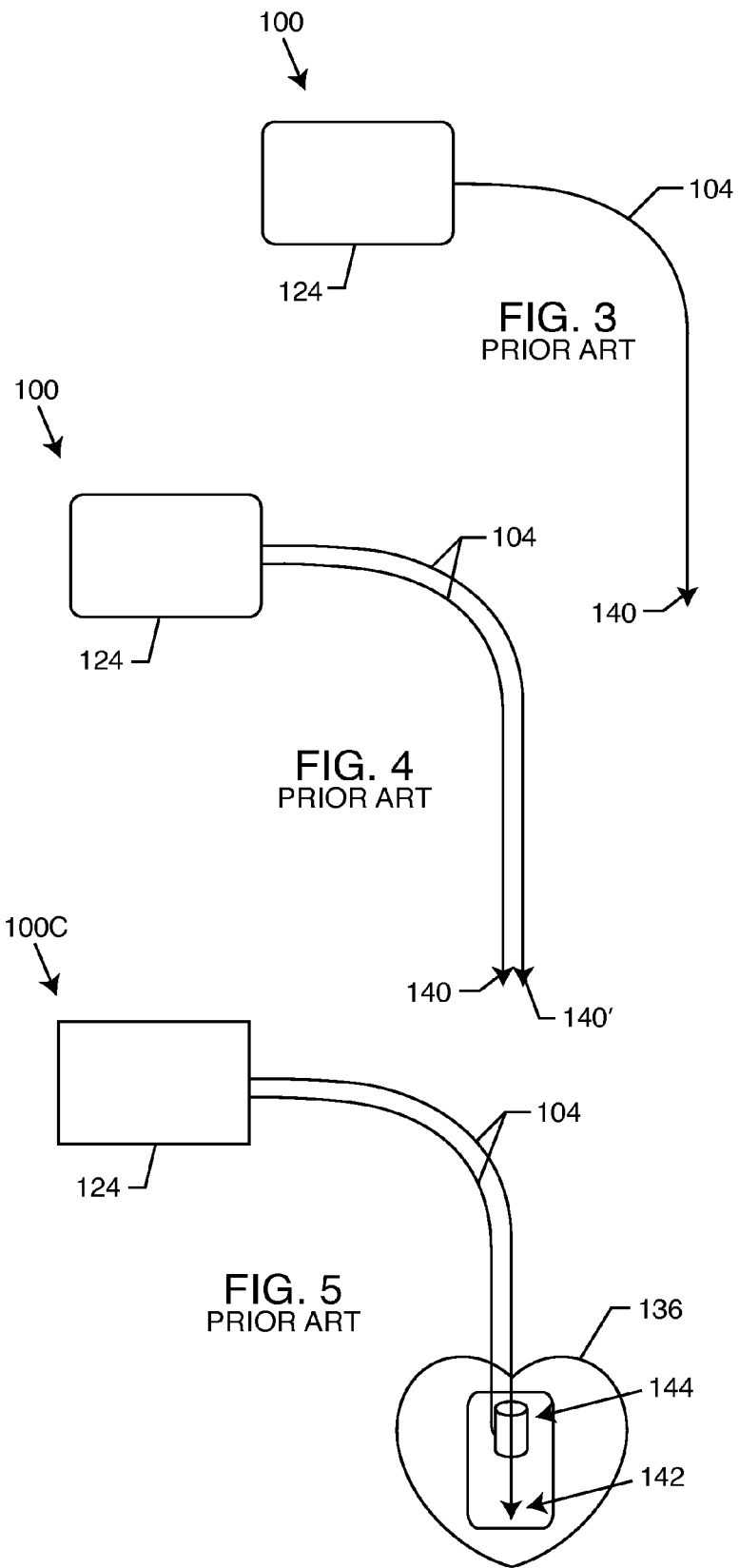

ACTIVE IMPLANTABLE MEDICAL SYSTEM HAVING EMI SHIELDED LEAD

FIELD OF THE INVENTION

This invention generally relates to the problem of energy induced onto implanted leads during medical diagnostic procedures such as magnetic resonant imaging (MRI). More specifically, the present invention relates to an implantable medical system comprised of an active implantable medical device (AIMD) and at least one lead extending exteriorly from a proximal end at or adjacent to the AIMD, to a biological sensing or stimulating electrode at a distal end.

BACKGROUND OF THE INVENTION

The radio frequency (RF) pulsed field of MRI can couple to an implanted lead in such a way that electromagnetic forces (EMFs) are induced in the lead. The amount of energy that is induced is related to a number of complex factors, but in general, is dependent upon the local electric field that is tangent to lead and the integral of the electric field strength along the lead. In certain situations, these EMFs can cause currents to flow into distal electrodes or in the electrode interface with body tissue. It has been documented that when this current becomes excessive, that overheating of said lead or its associated electrode or overheating of the associated interface with body tissue can occur. There have been cases of damage to such body tissue which has resulted in loss of capture of cardiac pacemaking pulses, tissue damage, severe enough to result in brain damage or multiple amputations, and the like.

Electromagnetic interference (EMI) is also a significant issue. It has been well demonstrated through various incidents and publications that an implanted lead can act as an antenna and pick up unwanted signals from the patient environment. In the past, there have been problems with microwave ovens, cell phones, and the like. Stray signals that are picked up on implanted leads can be coupled to the interior of the AIMD and interfere with sensitive electronic circuits. In cardiac pacemakers, instances of EMI being detected as normal cardiac rhythms have resulted in pacemaker inhibition which can be life-threatening.

MRI is one of medicine's most valuable diagnostic tools. MRI is, of course, extensively used for imaging, but is also used for interventional medicine (surgery). In addition, MRI is used in real time to guide ablation catheters, neurostimulator tips, deep brain probes and the like. An absolute contraindication for pacemaker or neurostimulator patients means that these patients are excluded from MRI. This is particularly true of scans of the thorax and abdominal areas. Because of MRI's incredible value as a diagnostic tool for imaging organs and other body tissues, many physicians simply take the risk and go ahead and perform MRI on a pacemaker patient. The literature indicates a number of precautions that physicians should take in this case, including limiting the power of the MRI RF Pulsed field (Specific Absorption Rate—SAR level), programming the pacemaker to fixed or asynchronous pacing mode, and then careful reprogramming and evaluation of the pacemaker and patient after the procedure is complete. There have been reports of latent problems with cardiac pacemakers or other AIMDs after an MRI procedure sometimes occurring many days later. Moreover, there are a number of recent papers that indicate that the SAR level is not entirely predictive of the heating that would be found in implanted leads or devices. For example, for magnetic resonance imaging devices operating at the same magnetic field strength and also at the same SAR level, considerable variations have been found relative to heating of implanted leads. It is speculated that SAR level alone is not a good predictor of whether or not an implanted device or its associated lead system will overheat.

There are three types of electromagnetic fields used in an MRI unit. The first type is the main static magnetic field designated $B_0$ which is used to align protons in body tissue. The field strength varies from 0.5 to 3.0 Tesla in most of the currently available MRI units in clinical use. Some of the newer MRI system fields can go as high as 4 to 5 Tesla. At the recent International Society for Magnetic Resonance in Medicine (ISMRM), which was held on 5-6 Nov. 2005, it was reported that certain research systems are going up as high as 11.7 Tesla and will be ready sometime in 2010. This is over 100,000 times the magnetic field strength of the earth. A static magnetic field can induce powerful mechanical forces and torque on any magnetic materials implanted within the patient. This would include certain components within the cardiac pacemaker itself and/or lead systems. It is not likely (other than sudden system shut down) that the static MRI magnetic field can induce currents into the pacemaker lead system and hence into the pacemaker itself. It is a basic principle of physics that a magnetic field must either be time-varying as it cuts across the conductor, or the conductor itself must move within a specifically varying magnetic field for currents to be induced.

The second type of field produced by magnetic resonance imaging is the pulsed RF field which is generated by the body coil or head coil. This is used to change the energy state of the protons and elicit MRI signals from tissue. The RF field is homogeneous in the central region and has two main components: (1) the electric field is circularly polarized in the actual plane; and (2) the H field, sometimes generally referred to as the net magnetic field in matter, is related to the electric field by Maxwell's equations and is relatively uniform. In general, the RF field is switched on and off during measurements and usually has a frequency of 21 MHz to 64 MHz to 128 MHz depending upon the static magnetic field strength. The frequency of the RF pulse for hydrogen scans varies by the Larmor equation with the field strength of the main static field where: RF PULSED FREQUENCY in MHz=(42.56) (STATIC FIELD STRENGTH IN TESLA). There are also phosphorous and other types of scanners wherein the Larmor equation would be different. The present invention applies to all such scanners.

The third type of electromagnetic field is the time-varying magnetic gradient fields designated $B_X$, $B_Y$, $B_Z$, which are used for spatial localization. These change their strength along different orientations and operating frequencies on the order of 1 kHz. The vectors of the magnetic field gradients in the X, Y and Z directions are produced by three sets of orthogonally positioned coils and are switched on only during the measurements. In some cases, the gradient field has been shown to elevate natural heart rhythms (heart beat). This is not completely understood, but it is a repeatable phenomenon. The gradient field is not considered by many researchers to create any other adverse effects.

It is instructive to note how voltages and electro-magnetic interference (EMI) are induced into an implanted lead system. At very low frequency (VLF), voltages are induced at the input to the cardiac pacemaker as currents circulate throughout the patient's body and create voltage drops. Because of the vector displacement between the pacemaker housing and, for example, the tip electrode, voltage drop across the resistance of body tissues may be sensed due to Ohms Law and the circulating current of the RF signal. At higher frequencies, the implanted lead systems actually act as antennas where voltages (EMFs) are induced along their length. These antennas are not very efficient due to the damping effects of body tissue; however, this can often be offset by extremely high power fields (such as MRI pulsed fields) and/or body resonances.

Magnetic field coupling into an implanted lead system is based on loop areas. For example, in an AIMD abandoned lead, there is a loop formed by the lead as it comes from the abandoned lead proximal tip to its distal tip electrode, for example, located in the right ventricle. The return path is through body fluid and tissue generally straight from the tip electrode in the right ventricle back up to the proximal end of the lead. This forms an enclosed area which can be measured from patient X-rays in square centimeters. Per ANSI/AAMI National Standard PC69, the average loop area is 200 to 225 square centimeters. This is an average and is subject to great statistical variation. For example, in a large adult patient with an abdominal pacemaker implant, the implanted loop area is much larger (around 400 square centimeters).

Relating now to the specific case of MRI, the magnetic gradient fields would be induced through enclosed loop areas. However, the pulsed RF fields, which are generated by the body coil, would be primarily induced into the lead system by antenna action. Subjected to RF frequencies, the lead itself can exhibit complex transmission line behavior.

At the frequencies of interest in MRI, RF energy can be absorbed and converted to heat. The power deposited by RF pulses during MRI is complex and is dependent upon the power (Specific Absorption Rate (SAR) Level) and duration of the RF pulse, the transmitted frequency, the number of RF pulses applied per unit time, and the type of configuration of the RF transmitter coil used. The amount of heating also depends upon the volume of tissue imaged, the electrical resistivity of tissue and the configuration of the anatomical region imaged. There are also a number of other variables that depend on the placement in the human body of the AIMD and the length and trajectory of its associated lead(s). For example, it will make a difference how much EMF is induced into a pacemaker lead system as to whether it is a left or right pectoral implant. In addition, the routing of the lead and the lead length are also very critical as to the amount of induced current and heating that would occur. The cause of heating in an MRI environment is twofold: (a) RF field coupling to the lead can occur which induces significant local heating; and (b) currents induced between the distal tip and tissue during MRI RF pulse transmission sequences can cause local Ohms Law heating in tissue next to the distal tip electrode of the implanted lead. The RF field of an MRI scanner can produce enough energy to induce RF voltages in an implanted lead and resulting currents sufficient to damage some of the adjacent myocardial tissue. Tissue ablation (destruction resulting in scars) has also been observed. The effects of this heating are not readily detectable by monitoring during the MRI. Indications that heating has occurred would include an increase in pacing threshold, venous ablation, Larynx or esophageal ablation, myocardial perforation and lead penetration, or even arrhythmias caused by scar tissue. Such long term heating effects of MRI have not been well studied yet for all types of AIMD lead geometries. There can also be localized heating problems associated with various types of electrodes in addition to tip electrodes. This includes ring electrodes or pad electrodes. Ring electrodes are commonly used with a wide variety of abandoned implanted device leads including cardiac pacemakers, and neurostimulators, and the like. Pad electrodes are very common in neurostimulator applications. For example, spinal cord stimulators or deep brain stimulators can include a plurality of pad electrodes to make contact with nerve tissue. A good example of this also occurs in a cochlear implant. In a typical cochlear implant there would be sixteen pad electrodes placed up into the cochlea. Several of these pad electrodes make contact with auditory nerves.

Just variations in the pacemaker lead length and implant trajectory can significantly affect how much heat is generated. A paper entitled, HEATING AROUND INTRAVASCULAR GUIDEWIRES BY RESONATING RF WAVES by Konings, et al., Journal of Magnetic Resonance Imaging, Issue 12:79-85 (2000), does an excellent job of explaining how the RF fields from MRI scanners can couple into implanted leads. The paper includes both a theoretical approach and actual temperature measurements. In a worst-case, they measured temperature rises of up to 74 degrees C. after 30 seconds of scanning exposure. The contents of this paper are incorporated herein by reference.

The effect of an MRI system on the leads of pacemakers, ICDs, neurostimulators and the like, depends on various factors, including the strength of the static magnetic field, the pulse sequence, the strength of RF field, the anatomic region being imaged, and many other factors. Further complicating this is the fact that each patient's condition and physiology is different and each lead implant has a different length and/or implant trajectory in body tissues. Most experts still conclude that MRI for the pacemaker patient should not be considered safe.

It is well known that many of the undesirable effects in an implanted lead system from MRI and other medical diagnostic procedures are related to undesirable induced EMFs in the lead system and/or RF currents in its distal tip (or ring) electrodes. This can lead to overheating of body tissue at or adjacent to the distal tip.

Distal tip electrodes can be unipolar, bipolar, multipolar and the like. It is very important that excessive RF current not flow at the interface between the lead distal tip electrode or electrodes and body tissue. In a typical cardiac pacemaker, for example, the distal tip electrode can be passive or of a screw-in helix type as will be more fully described. In any event, it is very important that excessive RF current not flow at this junction between the distal tip electrode and for example, myocardial or nerve tissue. Excessive current at the distal electrode to tissue interface can cause excessive heating to the point where tissue ablation or even perforation can occur. This can be life threatening for cardiac patients. For neuro-stimulator patients, such as deep brain stimulator patients, thermal injury can cause permanent disability or even be life threatening. Similar issues exist for spinal cord stimulator patients, cochlear implant patients and the like.

A very important and life-threatening problem is to be able to control overheating of implanted leads during an MRI procedure. A novel and very effective approach to this is to first install parallel resonant inductor and capacitor bandstop filters at or near the distal electrode of implanted leads. For cardiac pacemaker, these are typically known as the tip and ring electrodes. One is referred to U.S. Pat. No. 7,363,090; US 2007/0112398 A1; US 2008/0071313 A1; US 2008/0049376 A1; US 2008/0024912 A1; US 2008/0132987 A1; and US 2008/0116997 A1, the contents of all of which are incorporated herein. The invention of US 2007/0112398 A1 relates generally to L-C bandstop filter assemblies, particularly of the type used in active implantable medical devices (AIMDs) such as cardiac pacemakers, cardioverter defibrillators, neurostimulators and the like, which raise the impedance of internal electronic or related wiring components of the medical device at selected frequencies in order to reduce or eliminate currents induced from undesirable electromagnetic interference (EMI) signals.

U.S. Pat. No. 7,363,090 and US 2007/0112398 A1 show resonant L-C bandstop filters placed at the distal tip and/or at various locations along the medical device leads or circuits. These L-C bandstop filters inhibit or prevent current from circulating at selected frequencies of the medical therapeutic device. For example, for an MRI system operating at 1.5 Tesla, the pulse RF frequency is 64 MHz, as described by the Larmor Equation for hydrogen. The L-C bandstop filter can be designed to resonate at or near 64 MHz and thus create a high impedance (ideally an open circuit) in the lead system at that selected frequency. For example, the LC bandstop filter, when placed at the distal tip electrode of a pacemaker lead, will significantly reduce RF currents from flowing through the distal tip electrode and into body tissue. The L-C bandstop filter also reduces EMI from flowing in the leads of a pacemaker, for example, thereby providing added EMI protection to sensitive electronic circuits. In general, the problem associated with implanted leads is minimized when there is a bandstop filter placed at or adjacent to its distal tip electrodes.

An implanted lead acts very much as like a transmission line. When one creates a very high impedance at the distal electrode to tissue interface by installation of a resonant bandstop filter as described in U.S. Pat. No. 7,038,900 and as further described in US 2007/0112398 A1, there is created an almost open circuit which is the equivalent of an unterminated transmission line. This causes a reflection of MRI induced RF energy back towards the proximal end where the AIMD (for example, a pacemaker) is connected. In order to completely control the induced energy in an implanted lead system, one must take a system approach. In particular, a methodology is needed whereby energy can be dissipated from the lead system at the proximal end in a way that does not cause overheating either at the distal electrode interface or at the proximal end cap. Maximizing energy transfer from an implanted lead is more thoroughly described in U.S. patent Ser. No. 12/686,137, the contents of which are incorporated herein by reference.

Accordingly, there is a need for attenuating the RF energy that can be induced onto or into an implanted lead system. Further, there is a need to provide shielding of an implanted lead that will reduce or prevent external electromagnetic fields from coupling energy to said implanted lead. There is also a need to provide shielding in order to help protect the circuits of an AIMD from EMI, such as those signals produced by microwave ovens, cell phones and other environmental emitters. Moreover, there is a need for providing passive network components for diverting energy from the lead to the shield which can then act as a large surface area energy dissipating surface. The present invention fulfills these needs and provides other related advantages.

SUMMARY OF THE INVENTION

The present invention resides in a lead which extends exteriorly from an active implantable medical device (AIMD), which is at least partially ensheathed within an electromagnetic interference (EMI) shield. The AIMD has a conductive equipotential surface to which the EMI shield may be conductively coupled. An impeding circuit may be provided for raising the high frequency impedance of the lead, and an energy diversion circuit may also be provided for conductively coupling the lead to the EMI shield.

More particularly, an implantable medical system comprises: (1) an active implantable medical device (AIMD); (2) at least one lead having a length exteriorly extending from a proximal end at or adjacent to the AIMD, to a biological sensing or stimulating electrode at a distal end; and (3) an electromagnetic interference (EMI) shield surrounding the at least one lead along at least a portion of the length thereof. The EMI shield may include an electrically conductive exterior surface suitable for long-term exposure to body tissues/fluids. Alternatively, an insulator may be provided which surrounds the EMI shield along its length.

Typically, the AIMD has a conductive equipotential surface, such as the biocompatible housing for the AIMD. The EMI shield may be conductively coupled to the AIMD equipotential surface. The EMI shield may comprise a plurality of EMI shields disposed along the length of the at least one lead. An adjacent pair of the plurality of EMI shields may be spread apart from one another. Further, the plurality of EMI shields may be conductively coupled to one another.

The at least one lead may comprise a plurality of leads, in which case the EMI shield may comprise a corresponding plurality of EMI shields.

A non-conductive insulator may be disposed between the lead and the EMI shield. The EMI shield may comprise a conductive heat-shrink tubing, a deposited thin film of conductive material utilizing typical industrial methods for applying such material such as physical vapor deposition or chemical vapor deposition, a conductive foil, wire, braid, mesh, circuit trace, or solid tubular material. Moreover, the EMI shield may comprise a conductive polymer, a conductive epoxy, carbon nano-fibers, nano-meshes or nano-threads, MP35N, iridium, platinum, titanium, chromium, Wolfram, tungsten, gold or copper. Further, the EMI shield may include one or more stress relief scores. The EMI shield may be radially spaced from the at least one lead and/or include a flex cable embodying the at least one lead and the EMI shield.

Typically, a hermetic feedthrough terminal is associated with the AIMD housing. The at least one lead would then extend through the hermetic feedthrough terminal exteriorly of the AIMD housing to a distal end.

An energy diversion circuit may conductively couple the at least one lead to the EMI shield. The energy diversion circuit may comprise a low pass filter such as a capacitor, an inductor, a Pi filter, a T filter, an LL filter, or an "n" element filter. Moreover, the energy diversion circuit may comprise at least one series resonant L-C trap filter.

The energy diversion circuit may also comprise a high pass filter which prevents low frequency gradient field-induced energy in the implanted lead or lead wire from passing through the diversion circuit to the energy dissipating surface. The high pass filter may comprise a capacitor, a resistor in series with the capacitor, or an L-C trap filter.

An impeding circuit may be provided for raising the high frequency impedance of the at least one lead. The impeding circuit will typically comprise an inductor or a bandstop filter.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 3 is a schematic illustration of a prior art AIMD with a unipolar lead;

FIG. 4 is a schematic illustration similar to FIG. 3, except that the prior art AIMD has bipolar lead conductors;

FIG. 5 is similar to FIG. 4, except that the bipolar lead terminates in a distal tip electrode and a distal ring electrode;

DETAILED DESCRIPTION OF THE PREFERRED EMBODIMENTS

Figure 1:
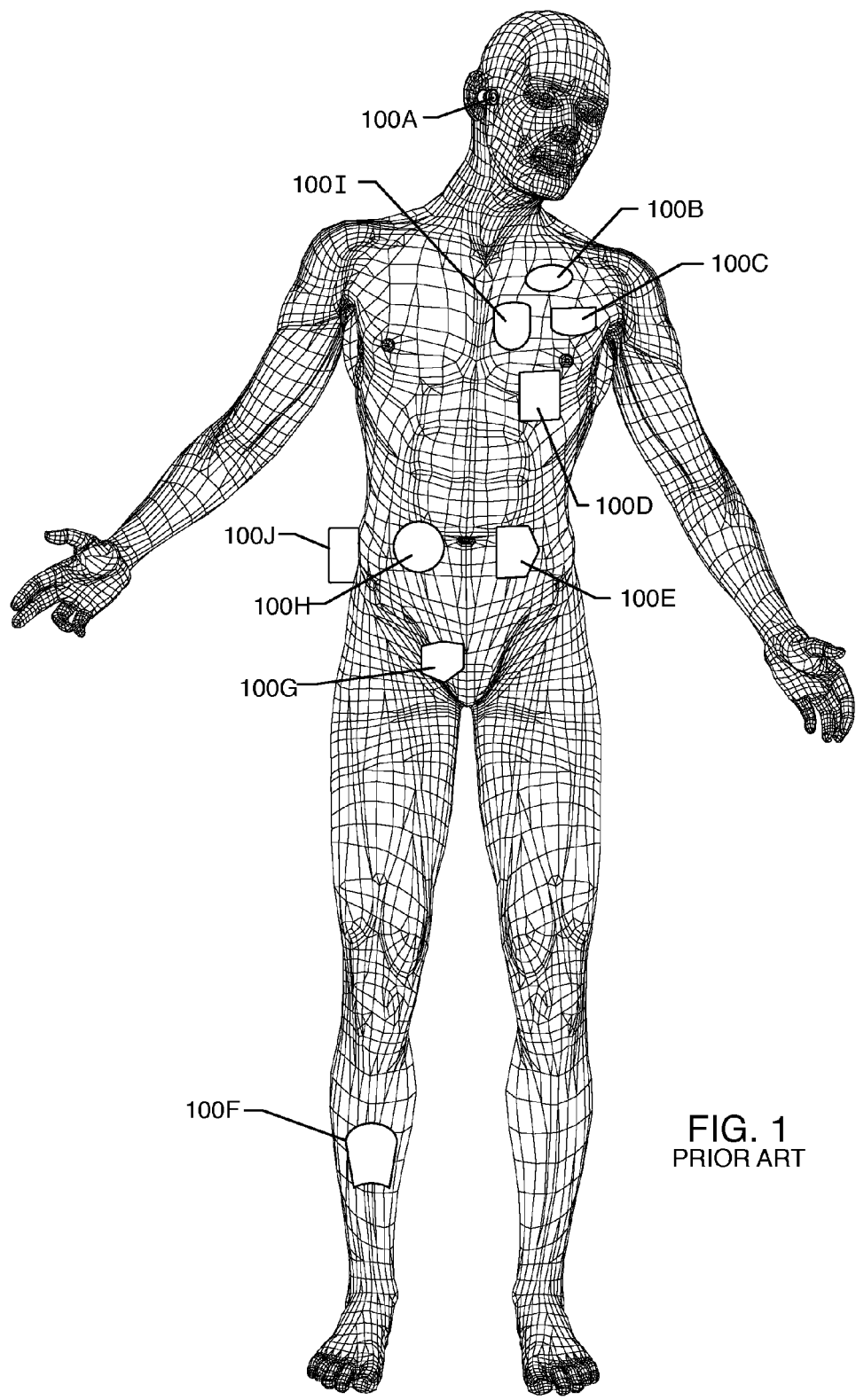
FIG. 1 is a wire-formed diagram of a generic human body showing a number of exemplary implanted medical devices.

As shown in the drawings for purposes of illustration, the present invention relates to a system for RF shielding of AIMD implanted leads to minimize heating and/or electromagnetic interference (EMI) in the presence of high power electromagnetic field environments. In a broad sense, the present invention comprises an active implantable medical system including an implanted lead having partial or total RF shielding. The implanted lead may be coaxial, rectangular, flat or other geometries. Furthermore, the implanted lead may consist of a number of internal conductors, such as a bipolar lead for cardiac pacemaker channel or even an eight or sixteen conductor spinal cord stimulator implanted lead. This is also known as a multichannel lead system.

In general, the shield of the present invention would surround all of the conductors in a particular implanted lead that is routed to a particular area of body tissue. For example, in a cardiac pacemaker application, there are often dual chamber bipolar conductors in the implanted lead. In a dual chamber pacemaker, one lead is typically routed to the right ventricle and the other to the right atrium. Each of these implanted leads, consisting of two conductors, would be individually shielded. Typically conforming to the shape of the leads, the shields of the present invention may be coaxial, flat, rectangular or any other geometry suitable for either tunneling or for transvenous insertion within the human body.

The shield of the present invention can also act as a large energy dissipating surface. Diverting circuits, consisting of either capacitors, low-pass filter, L-C trap filters or high-pass filters, can be used to divert energy from an implanted lead to its surrounding shield. The shield, in a preferred embodiment, is in contact with body tissue whereby induced RF energy from the lead is diverted to the shield, which in turn acts as an energy dissipating surface. US 2010/002300 A1 is incorporated herein by reference.

Implanted leads have both a characteristic impedance and also act as a transmission line. They tend to effectively couple energy from an external electromagnetic interference emitter as a function of their wavelength. This also varies with lead trajectory, design and other factors. However, when one is only concerned with particular frequency ranges, for example the RF pulse frequency of MRI, it is not necessary to shield the entire lead. In this regard, one could shield a significant portion of the lead so that the exposed (unshielded) portion of the lead was significantly less than a half or a quarter wavelength in body tissue. This makes the remaining lead a very inefficient antenna and therefore it would only pick up a very small amount of induced energy. Accordingly, in accordance with the present invention, one could shield the entire implanted lead, a portion of the implanted lead or even segments of the implanted lead. By shielding segments of the implanted lead, one would break up its resonant lengths thereby making it a very ineffective antenna over a broad range of frequencies.

The shields of the present invention can be a solid conductor, wound spiral conductors, meshes, tubing or the like. In the preferred embodiment, the shield would present a fairly homogenous conductive surface such that it would effectively reflect and/or absorb incident electromagnetic fields. However, complete shielding is really not necessary. Accordingly, the shield could be loosely woven such that only a portion of the electromagnetic interference was intercepted.

The invention further resides in a combination of shields with one or more impeding circuits which could also be optimally combined with one or more diversion circuits. The impeding circuits typically would consist of either inductors or L-C parallel resonant-bandstop filters. The diversion circuits would typically consist of a capacitor, a multi-element low-pass filter, a high-pass filter, or an L-C trap filter. The operation of impeding circuits and diversion circuits is more thoroughly described in US 2010,002300 A1 and U.S. patent application Ser. No. 12/686,137, which are incorporated by reference. In a particularly preferred embodiment, the shield of the present invention is used in combination with an impeding circuit known as a bandstop filter. The bandstop filter has a Q and 3-dB bandwidth such that, at resonance, it offers attenuation of at least 10 dB over a range of MRI RF pulsed frequencies at least 100 kHz wide.

In the case where bandstop filters are installed at or near the distal electrode of an implanted lead, the RF energy induced by the MRI pulse field is inhibited from flowing into body tissues and thereby being dissipated. However, even when distal electrode bandstop filters are used, that energy still resides in the lead system. In other words, by preventing this induced energy from flowing to sensitive tissues at distal electrode interfaces, a great deal has been accomplished; however, it is still important to carefully dissipate the remaining energy that's trapped in the lead system.

In order to provide optimal decoupling of RF energy from an implanted lead to the energy dissipating surface of a shield, one should consider Thevenin's maximum power transfer theorem. When one has an ideal source, consisting of a voltage source and a series impedance, this is known as a Thevenin Equivalent Source Circuit. It is well known in electrical engineering that to transfer maximum power to a load that the load impedance must be equal to the source impedance. If the source impedance is completely resistive, for example, 50 ohms, then to transfer maximum power, the load impedance would have to be 50 ohms. When the source impedance is reactive, then to transfer maximum power to another location, the load impedance should have the opposite sign of reactance and the same impedance and resistance. Referring to a typical implanted lead system, the implanted leads typically appear inductive. Accordingly, having a capacitive energy diversion circuit to couple energy from the lead conductors to the EDS shield surface, one has at least some cancellation of these imaginary impedance factors. In electrical engineering, the inductance of the lead would be denoted by $+j\omega L$. The impedance of the capacitor, on the other hand, is a $-j/\omega C$ term.

FIG. 1 illustrates various types of active implantable medical devices referred to generally by the reference numeral 100 that are currently in use. FIG. 1 is a wire formed diagram of a generic human body showing a number of exemplary implanted medical devices. 100A is a family of implantable hearing devices which can include the group of cochlear implants, piezoelectric sound bridge transducers and the like. 100B includes an entire variety of neurostimulators and brain stimulators. Neurostimulators are used to stimulate the Vagus nerve, for example, to treat epilepsy, obesity and depression. Brain stimulators are similar to a pacemaker-like device and include electrodes implanted deep into the brain for sensing the onset of the seizure and also providing electrical stimulation to brain tissue to prevent the seizure from actually happening. 100C shows a cardiac pacemaker which is well-known in the art. 100D includes the family of left ventricular assist devices (LVAD's), and artificial hearts, including the recently introduced artificial heart known as the Abiocor. 100E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted leadwires. 100F includes a variety of implantable bone growth stimulators for rapid healing of fractures. 100G includes urinary incontinence devices. 100H includes the family of pain relief spinal cord stimulators and anti-tremor stimulators. 100H also includes an entire family of other types of neurostimulators used to block pain. 100I includes a family of implantable cardioverter defibrillator (ICD) devices and also includes the family of congestive heart failure devices (CHF). This is also known in the art as cardio resynchronization therapy devices, otherwise known as CRT devices.

The various types of active implantable medical devices (AIMDs) illustrated in FIG. 1, generally represents any type of AIMD that is considered a "long-term" implant. This is in direct contrast to things like probes or catheters or surgical devices that are "short-term" body insertions. For example, a probe or catheter is typically used in a cath-lab situation wherein it is temporarily inserted through a femoral (or other) artery where the entire procedure lasts minutes or at most a few hours. On the other hand, a long-term implant, such as a cardiac pacemaker, is generally designed to be implanted in the human body for many years. There are significant differences in the art between a short-term and a long-term implant. For example, for a long-term implant, one has to worry greatly about the long-term biocompatibility, toxicity and even the hermeticity of the implant. In contrast, a probe, catheter or temporary loop recorder need only operate or be reliable for a matter of minutes or even hours. In general, a short-term implant is often considered to be a disposable device. In addition, the FDA regulatory approval processes for long-term implants is significantly different and involves much more rigorous testing and product safety and reliability criteria. The FDA Center for Devices and Radiological Health (FDA-CDRH) is the responsible regulatory agency for long-term cardiac implants. As used herein, the term AIMD is construed to be a long-term implant.

Referring to US 2003/0050557, Paragraphs 79 through 82, the contents of which are incorporated herein, metallic structures, particularly leads, are described that when placed in MRI scanners, can pick up high electrical fields which results in local tissue heating. This heating tends to be most concentrated at the ends of the electrical structure (either at the proximal or distal lead ends). This safety issue can be addressed using the disclosed systems and methods of the present invention. A significant concern is that the distal electrodes, which are in contact with body tissue, can cause local tissue burns.

As used herein, the lead means an implanted lead, including its electrodes that are in contact with body tissue. In general, for an AIMD, the term lead means the lead that is outside of the AIMD hermetically sealed housing and is implanted or directed into body tissues. The term conductor or leadwire as used herein, refers to the individual leads, filers or channels that are inside of the implanted lead. These may be unipolar, bipolar, multipolar or the like. Throughout, the term lead or leadwire generally refers to leads or leadwires that are external to the housing of the active implantable medical device. These leads tend to have a proximal end, which is at or adjacent to the AIMD, and a distal end, which typically includes one or more electrodes which are in contact with body tissue.

Figure 2:
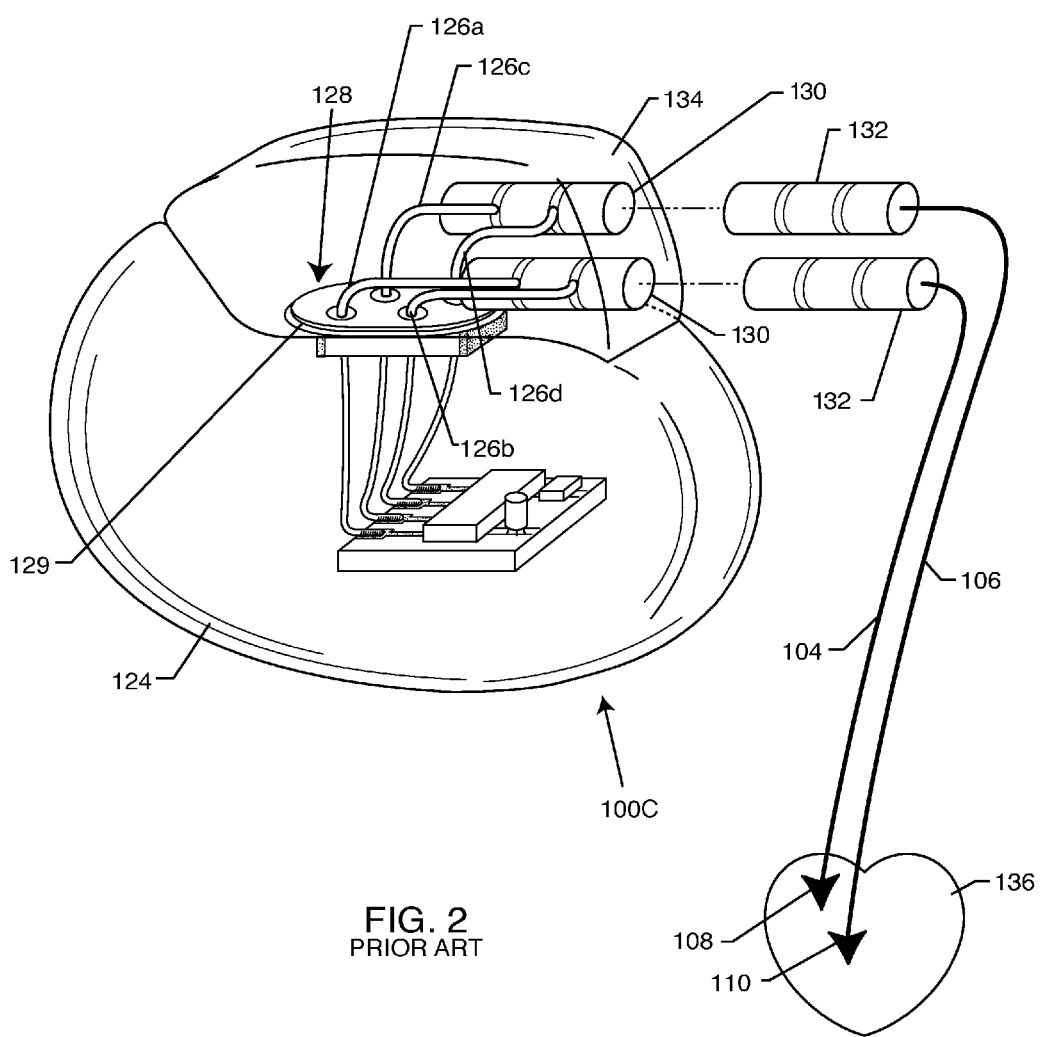
FIG. 2 illustrates an exemplary prior art cardiac pacemaker with the leads schematically shown extending to the patient's heart.

Referring now to FIG. 2, a prior art active implantable medical device (AIMD) 100 is illustrated. In general, the AIMD 100 could, for example, be a cardiac pacemaker 100C which is enclosed by a titanium or stainless steel conductive housing 124. The conductive housing 124 is hermetically sealed and contains a battery and electronic circuits, however, there is a point where conductors 126a, 126b, 126c and 126d must ingress and egress in non-conductive relationship relative to the housing 124. This is accomplished by providing a hermetic terminal assembly 128. Hermetic terminal assemblies 128 are well known and generally consist of a ferrule 129 which is laser welded to the titanium housing 124 of the AIMD 100C. In FIG. 2, four conductive leadwires 126a-126d are shown for connection to a corresponding number of leads, such as the illustrative bipolar leads 104 and 106 shown for coupling to the connector receptacles 130. In this configuration, the two leads 104, 106 comprise four conductors 126a-126d in a typical dual chamber bipolar cardiac pacemaker application. It should be noted that each of the bipolar leads 104 and 106 have a pair of conductors or leadwires associated with them. Each lead 104, 106 has bipolar electrodes wherein one conductor is routed to the tip electrode and the other is routed to the ring electrode in locations 108 and 110.

Connectors 132 are commonly known as IS-1 connectors and are designed to plug into mating receptacles 130 on a header block 134 mounted on the pacemaker housing 124. These are low voltage (pacemaker) lead connectors covered by an International Standards Organization (ISO) standard IS-1. Higher voltage devices, such as implantable cardioverter defibrillators, are covered by a standard known as the ISO DF-1. A newer standard had been published that integrates both high voltage and low voltage connectors into a new miniature quadpolar connector series known as the ISO IS-4 standard. Leads plugged into these connectors are typically routed in a pacemaker or ICD application into the right ventricle and right atrium of the heart 136.

In the following description, functionally equivalent elements shown in various embodiments will often be referred to utilizing the same reference number.

Referring once again to the prior art AIMD 100, such as the cardiac pacemaker 100C in FIG. 2, generally such AIMDs have primary batteries that have a limited lifetime. It is very common in the art, since the AIMD is laser welded and hermetically sealed, that when battery replacement is due, the entire AIMD is replaced. If there is nothing wrong with the implanted leads 104 and 106, they are generally reused. However, in many cases, there are lead defects, poor impedance characteristics, or even breaks or abrasions in a lead that cause the physician to remove or abandon them and insert new leads. It is a relatively easy matter to insert new leads endocardially in parallel with the existing leads. These new leads are then connected to a new AIMD, such as a new cardiac pacemaker.

FIG. 3 illustrates a prior art AIMD 100 with a unipolar lead 104. This means that the lead only has one internal conductor or leadwire. The distal electrode 140 acts as one electrode and the AIMD housing 124 acts as a return electrode. Electromagnetic interference is typically induced to such a lead by antenna action or can be induced by current circulating in the human body resulting in a voltage drop between the distal electrode 140 and the AIMD housing 124. Unipolar lead systems, in general, tend to be very sensitive to EMI which can interfere with AIMD electronics.

FIG. 4 is very similar to FIG. 3 except that the prior art AIMD 100 has bipolar lead conductors 140 and 140'. These are typically routed in one implanted lead 104. In this case, there is not much separation distance between the electrodes 140 and 140'. This would be typical in a neurostimulator application which can have as many as eight, sixteen, twenty-four or any more lead conductors and associated distal electrodes.

FIG. 5 illustrates a variation of the prior art bipolar AIMD lead shown in FIG. 4. Illustrated is a cardiac pacemaker 100C with a bipolar lead 104 which terminates in a distal tip electrode 142 and a distal ring electrode 144. The distal tip electrode 142, in the prior art, can have tines which grasp cardiac traebuclar tissue in the human heart, or can be bent back, such as in the atrial chamber. The ring electrode 144 generally floats in the blood pool. The separation distance between the tip electrode 142 and the ring electrode 144 is very important to determine far-field and near-field electrical sensing activities of the myocardium in the heart. In addition, pacing pulses are generated between the tip electrode 142 and the ring electrode 144. Bipolar systems, such as illustrated in FIG. 5, tend to be less susceptible to differential mode interference. It is important that the area between the tip electrode 142 and the ring electrode 144 not be shielded so that they can properly function and sense biologic activity.

Figure 6:
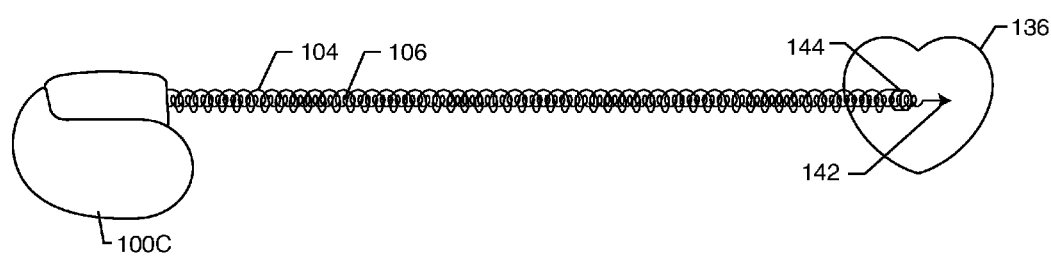
FIG. 6 is similar to FIG. 5, except that the bipolar lead wires are coaxially wound around one another.

FIG. 6 is very similar to FIG. 5 except that the bipolar leadwires 104, 106 are coaxially wound around one another. There is an inner filer and a coaxial outer filer which connect to the tip electrode 142 and the ring electrode 144 that are in contact with the human heart 136. For simplicity, in subsequent drawings the leads 104, 106 are generally shown by straight lines. It will be apparent that all of the shielding principles of the present invention are applicable to all types of lead geometries, including filer, bifiler, coaxial, ribbon leads, flex cables and the like.

Figure 7:
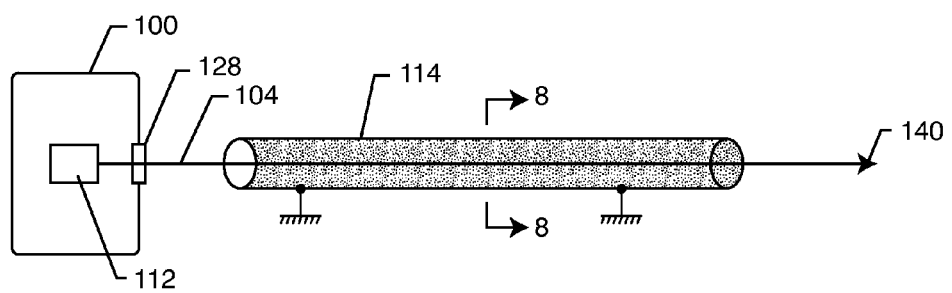
FIG. 7 is a schematic illustration similar to FIG. 3, wherein an electromagnetic interference (EMI) shield surrounds the lead along at least a portion of the length thereof in accordance with the present invention.

FIG. 7 illustrates a unipolar conductor 104 similar to FIG. 3 that is routed through the hermetic terminal 128 of an AIMD 100. The lead 104 is connected to an internal circuit board 112 of the AIMD. The lead 104 is at least partially shielded 114 over its length before its routed to a distal electrode 140. The shield 114 can either be an electric shield, a magnetic shield or both. Shielding materials include MP35N, iridium, platinum, titanium, chromium, Wolfram, tungsten, gold or copper. The shield 114 could also be made of various nano deposited materials. Preferably, the shield 114 is non-toxic, biocompatible and non-magnetic so as to be more compatible in an MRI environment. The shield 114 or its coating may be scored to allow stress relief. In general, the score marks or holes would be smaller than the wavelengths of an MRI pulsed RF field in the medium.

Figure 8:
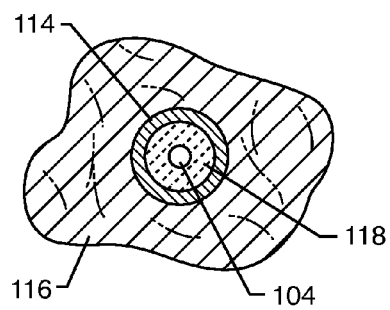
FIG. 8 is an enlarged sectional view taken generally along the line 8-8 from FIG. 7, illustrating that the EMI shield may be placed in direct contact with body tissues and fluids.

FIG. 8 illustrates a cross-sectional view taken generally along line section 8-8 from FIG. 7. Shown is an outer conductive shield 114 which is in direct contact with body tissues and fluids 116. Body fluids could include human tissues, lymph nodes, blood and its components, or the like. The leadwire or conductor 104 is insulated from the shield 114 by insulation material 118. Material 118 may have specific dielectric properties.

Figure 9:
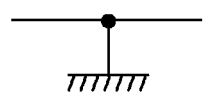
FIG. 9 illustrates a defined ground symbol that is used in the drawings to designate when the EMI shield is in direct contact with body fluid.

FIG. 9 illustrates a defined ground symbol which indicates when the shield of the present invention has no outer insulation and is in direct contact with body fluids 116. This symbol will be used herein when the shield does directly contact body fluid.

Referring once again to FIG. 8, the various lead 104 layers could be formed by step deposition. In other words, metal, insulator, metal, insulator, etc. The insulator 118 could be PTFE or related biocompatible material. The shield 114 could be co-deposited or it could be impregnated meshes. The shield 114 could also be formed of conductive polymers, conductive epoxies, carbon nano-fibers, nano-meshes, and nano-threads. The conductive shield 114 could also be formed of conductive heat shrink tubing. These may be combined or impregnated with a silicone/polyurethane tubing to change the RF absorption coefficients, which would change the loss tangent.

Figure 10:
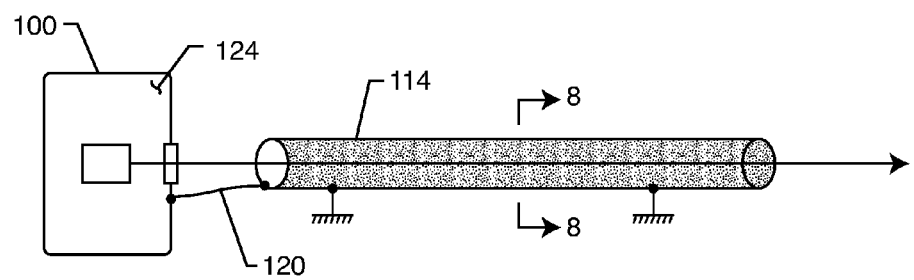
FIG. 10 is a schematic illustration similar to FIG. 7, except that the EMI shield is conductively coupled to a housing for the AIMD.

FIG. 10 is very similar to FIG. 7 except that the shield 114 has been connected with a wire 120 to the conductive housing 124 of the AIMD 100. In this way, the shield 114 is terminated to the conductive housing 124 of the AIMD 100 such that energy will be desirably shunted from the shield 114 to the AIMD housing 124.

Figure 11:
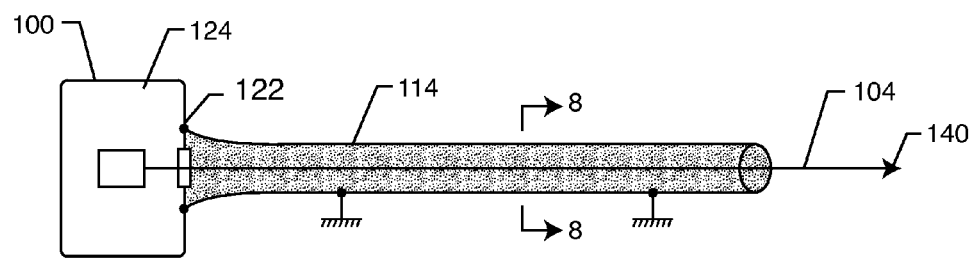
FIG. 11 is similar to FIG. 10, except that the EMI shield extends to and is conductively coupled to the AIMD housing.

FIG. 11 is very similar to FIG. 10 except that the individual leadwire 120 has been replaced by a continuous connection 122 of the shield 114 to the AIMD housing 124. This is known as a single end terminator to EMI shielded cable and is extremely effective at preventing the induction of unwanted RF energy onto the implanted lead 104 and/or its distal electrode 140.

Figure 12:
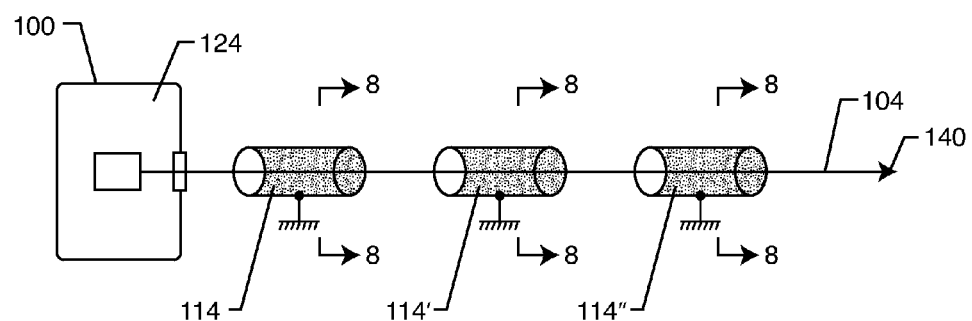
FIG. 12 is similar to FIG. 10, except that the EMI shield is broken into multiple segments.

FIG. 12 shows the shield 114 of FIG. 10 broken into multiple segments 114, 114' and 114". There can be any number of segments 114n. The presence of the multiple shield segments makes the implanted lead 104 a very ineffective antenna at high frequencies, such as MRI RF pulse frequencies. This means it will couple far less energy to the lead and its conductors in an MRI or other high powered electromagnetic field environment.

Figure 13:
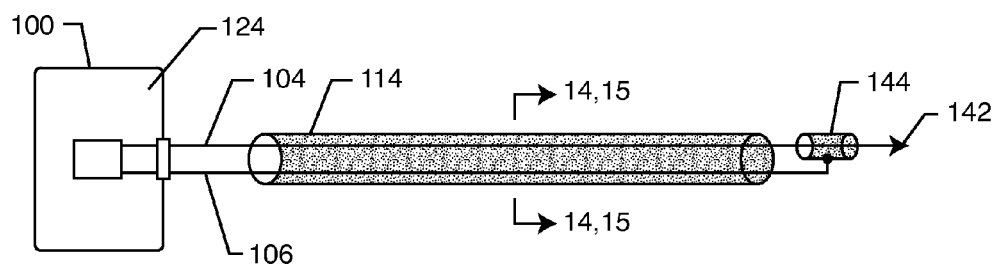
FIG. 13 is similar to FIG. 10, except in this case the EMI shield is surrounded by an insulation sheath.

FIG. 13 is similar to FIG. 10 except that in this case, the novel EMI shield 114 is surrounded by a insulation sheath 118. Another difference is this is a bipolar system wherein the lead comprises leadwires 104 and 106 which are surrounded by a single shield 114. Shown are a typical pacemaker tip electrode 142 and a ring electrode 144.

Figure 14:
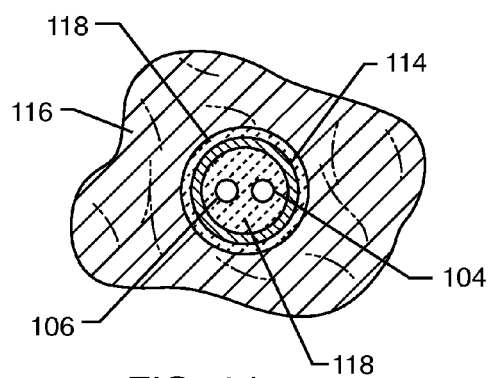
FIG. 14 is an enlarged sectional view taken generally along the line 14-14 from FIG. 13.

FIG. 14 is a cross-sectional view taken generally along section 14-14 from FIG. 13. Shown are the two bipolar lead conductors 104 and 106. These are separated from the conductive shield 114 by a dielectric insulating material 118. There is also an insulative sheath 118 which circumferentially surrounds the conductive shield 114. In this case, the shield 114 therefore is not in direct contact with body fluids 116. Therefore, in this embodiment the shield 114 does not act as an efficient energy dissipating surface to body fluid.

Figure 15:
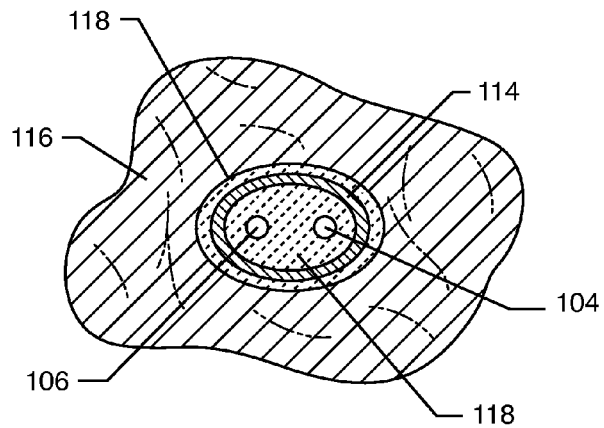
FIG. 15 is a cross-sectional view similar to FIG. 14, except that the cross-sectional shape is elliptical rather circular.

FIG. 15 is very similar to FIG. 14 except the shape is elliptical rather than circular. It will be apparent to those skilled in the art that the cross-sectional shape could be of any geometry, including flat, rectangular and the like.

Figure 16:
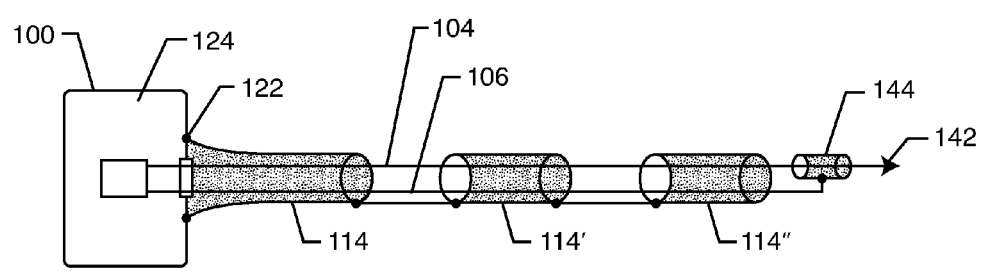
FIG. 16 is similar to FIG. 13, except that the lead has been broken into segments which are interconnected and are conductively coupled to the AIMD housing.

FIG. 16 is similar to FIG. 13 except the lead has been broken into segments which are interconnected and all connected to the housing 124 of the AIMD via connection 122. In a preferred embodiment, the segments shown in FIG. 16 would be continuous in that the bulk of the lead would be shielded up to an area close to its ring and tip electrodes. Since these particular shields are not in direct contact with body tissue, it's very important that they, in a preferred embodiment, be connected to the conductive housing 124 of the AIMD 100. In this way, energy induced on the shield 114 can be conductively coupled to the relatively large surface area of the AIMD housing 124 where the energy will be dissipated into body tissues with a miniscule temperature rise.

Figure 17:
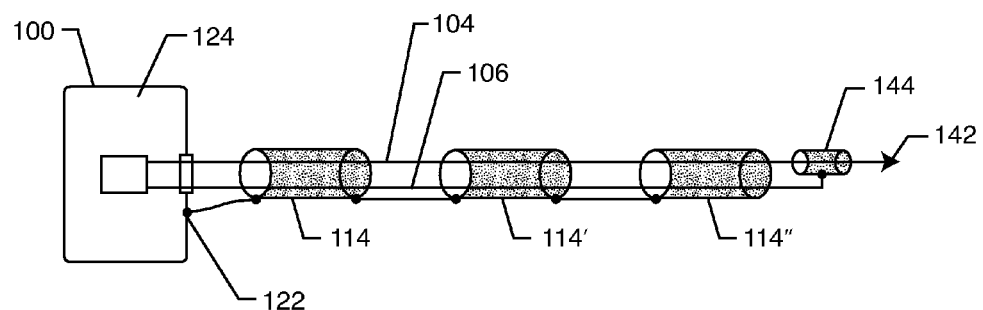
FIG. 17 is similar to FIG. 16, except that the individual segments have been connected to each other through the addition of a third wire which is, in turn, connected to the AIMD housing.

FIG. 17 is very similar to FIG. 16 except the individual segments have been connected to each other through the addition of third wire and in turn, connected to the AIMD housing 124 at point 122.

Figure 18:
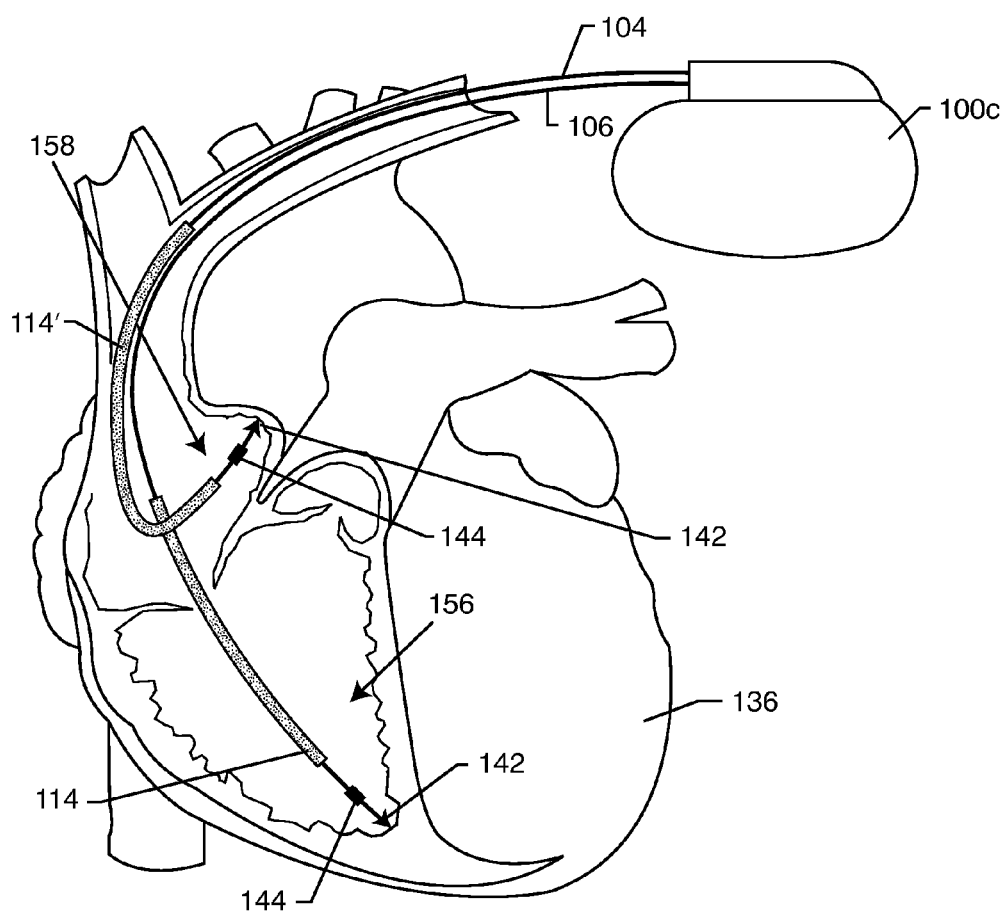
FIG. 18 is a cross-sectional view of a human heart with a cardiac pacemaker connected to two bipolar leads each at least partially ensheathed by the EMI shield in accordance with the present invention.

FIG. 18 is a cross-sectional view of a human heart with a cardiac pacemaker 100C connected to two bipolar leads 104 and 106. Each of the bipolar leads 104 and 106 have two internal conductors which are connected to distal tip 142 and ring electrodes 144. Shown shaded are partial shields 114 and 114'. In this case, they circumferentially surround about 50% of the length of each of the implanted leads. As can be seen, one of the leads is implanted into the right ventricle 156 and the other lead is implanted into the right atrium 158. The right atrial lead has tip electrode 142 and ring electrode 144. The other bipolar lead has a distal tip electrode 142 implanted in the right ventricular apex and a ring electrode 144.

Figure 19:
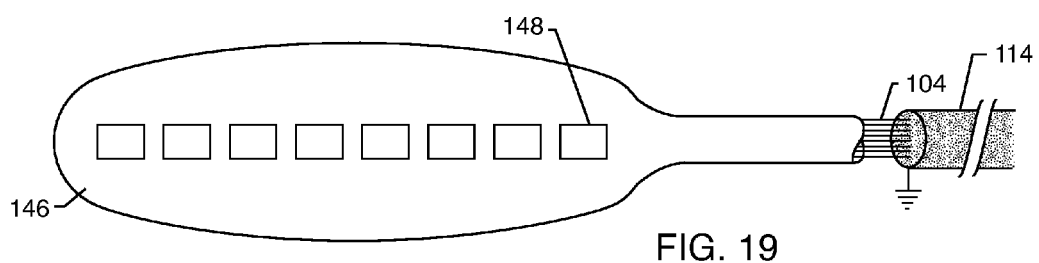
FIG. 19 illustrates the distal end of a typical neurostimulator paddle electrode.

FIG. 19 illustrates the distal end of a typical neurostimulator paddle electrode 146, which in this case has eight electrode contact points 148. Shown is a shield 114 of the present invention which shields the implanted lead conductors 104 in accordance with the present invention.

Figure 20:
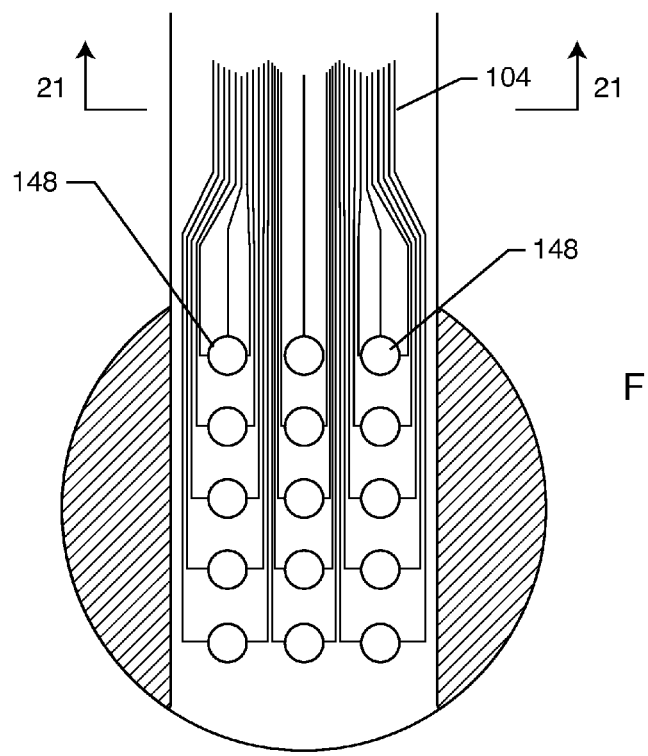
FIG. 20 is similar to FIG. 19, except that the paddle lead has been replaced with a series of flex cable electrodes.

FIG. 20 is similar to FIG. 19 except the paddle lead 146 has been replaced with a series of flex cable electrodes 148.

Figure 21:
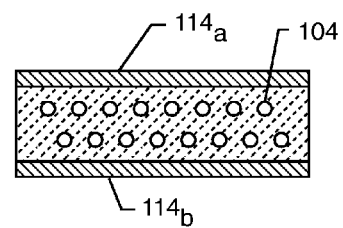
FIG. 21 is an enlarged sectional view taken generally along the line 21-21 from FIG. 20.

FIG. 21 is a sectional view taken generally along section 21-21 from FIG. 20. Shown are shields 114a and 114b which are sandwiched above and below the conductors 104 that are routed to electrodes 148. The shields 114a and 114b leads can be in direct contact with body tissue and/or connected to the AIMD housing as previously described in FIGS. 7 to 18. In a preferred embodiment, the shields 114 would completely peripherally surround the implanted leadwires 104. However, just shielding the top and bottom of a flex cable lead would provide a very high degree of attenuation to external electromagnetic fields.

Figure 22:
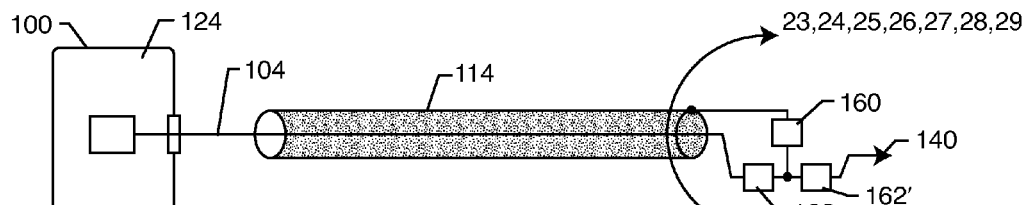
FIG. 22 is a schematic illustration similar to FIG. 7, wherein the distal tip electrode has an associated diversion circuit and/or one or more impeding circuits.

FIG. 22 is very similar to FIG. 7 except the distal electrode 140 has associated with it a diversion circuit 160 and/or one or more impeding circuits 162 and 162'. As will be described, the diversion circuits 160 generally consist of multi-element low pass filters, including single element capacitors. They could also be L-C trap filters or high-pass filters. The impeding elements, in general, can include one or more inductors, or parallel resonant L-C bandstop filters. The impeding circuits 162 and diversion circuits 160 generally comprise passive variable frequency reactive elements. That is, their impedance changes with frequency and they are therefore frequency selective.

Figure 23:
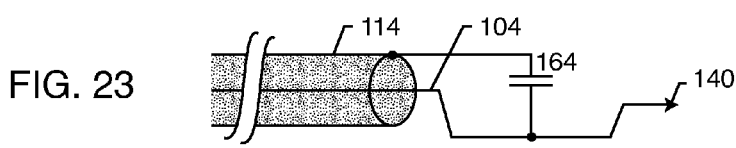
FIG. 23 illustrates that the diversion circuit of FIG. 22 may comprise a simple capacitor.

FIG. 23 is an illustration of a diversion circuit 160 taken from FIG. 22 wherein the diverter is a simple capacitor 164. At high frequency, the capacitor 164 tends to look like a short circuit and thereby divert induced RF energy away from the implanted lead conductor and to the circumferentially surrounding shield 114. This has the desired effect of decoupling RF energy away from the distal electrode 140 thereby providing a high degree of protection to body tissues.

Figure 24:
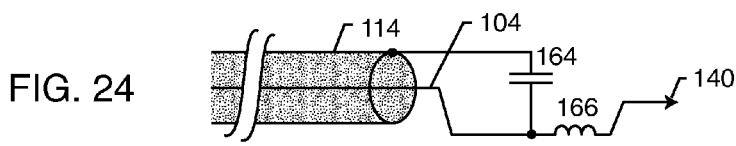
FIG. 24 is similar to FIG. 23, except that an impeding element L has been added in combination with the diverter element.
Figure 25:
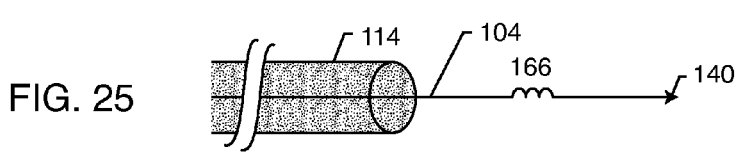
FIG. 25 is similar to FIGS. 23 and 24, illustrating that in some cases only an impeder element L is needed.

FIG. 24 is very similar to FIG. 23 except that an impeding element 166 has been added in combination with the diverter element 164. This impeding element 166 can be used by itself without the diverter 164 or in combination. When used in combination it forms an L filter. At high frequencies, the inductor 166 tends to look like a high impedance thereby improving the efficiency of decoupling energy through capacitor 164 to the shield 114. In one preferred embodiment, only the impeder 166 is needed. This preferred embodiment is shown in FIG. 25, wherein an impeder inductor 166 is used in combination with shield 114.

Figure 26:
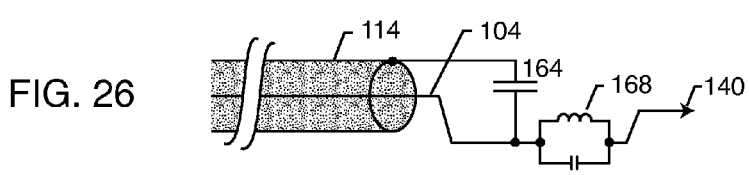
FIG. 26 is similar to FIG. 24, showing the impeding element in the form of a bandstop filter.

FIG. 26 is another variation of the general schematic shown in FIG. 22, wherein the diverter 164 is used in combination with a bandstop filter 168.

Figure 27:
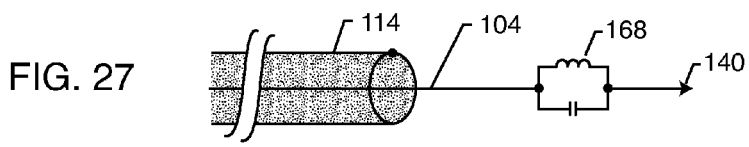
FIG. 27 is similar to FIG. 25, illustrating that the impeding element may comprise a bandstop filter.

FIG. 27 illustrates a particularly preferred embodiment which combines an impeder element known as a parallel resonant inductor/capacitor bandstop filter 168. The bandstop filter 168 presents a very high impedance at selected MRI frequencies and works in concert with the shield 114 to prevent RF currents from flowing into adjacent body tissues via electrode 140.

Figure 28:
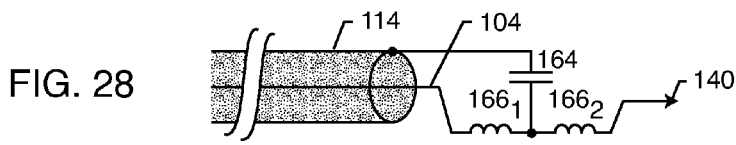
FIG. 28 is similar to FIG. 24, illustrating another variation including two impeders.

FIG. 28 is yet another variation where a capacitor 164 is used in combination with two impeders consisting of two inductors 1661 and 1662. This is otherwise known in the prior art as a T low-pass filter.

Figure 29:
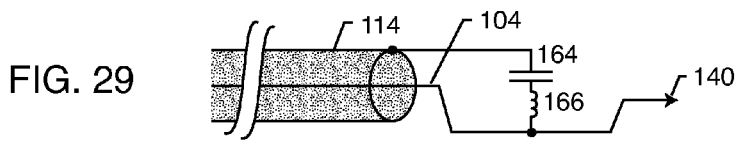
FIG. 29 is similar to FIG. 23, wherein the diversion circuit consists of an inductor in series with a capacitor, otherwise known as an L-C trap filter.

FIG. 29 illustrates a diversion circuit consisting of an inductor 166 in series with a capacitor 164, which is otherwise known as an L-C trap filter. When these two components are at resonance, they tend to form a short circuit. This is very important for diverting high frequency energy over a band of selected band frequencies from the implanted lead 104 to the shield 114.

Figure 30:
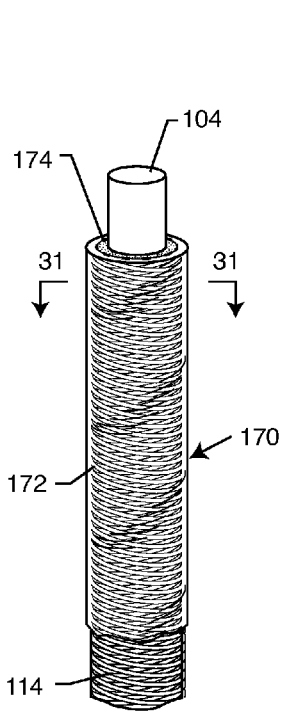
FIG. 30 illustrates an exemplary EMI shield formed of reinforced polyimide tubing.
Figure 31:
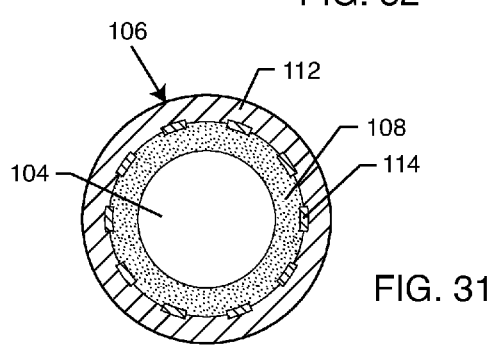
FIG. 31 is an enlarged sectional view taken generally along the line 31-31 from FIG. 30.

FIG. 30 illustrates a reinforced polyimide tubing 170. As shown in FIG. 31 which is taken from Section 31-31 from FIG. 30, the typical construction consists of a substrate layer 174, a braided or coiled metallic shield layer 114 and an exterior layer 172. The substrate 174 and exterior layer 172 are insulative wherein the embedded braided or coiled layer 114 is a conductive metal. In a particularly preferred embodiment, the insulative exterior layer 172 would be eliminated such that the conductive shield 114 would be in direct contact with body fluid. Since the conductive shield 114 has a relatively very large surface area, RF energy can be conducted in the body tissues without resulting in significant temperature rise. This is further described in both U.S. patent application Ser. No. 12/686,137 and US 2010/002300 A1, both of which are herein incorporated by reference. The most common braid coil 114 material is 304V stainless steel. Other metallic materials can also be used. The embedded braid coil 114 accomplishes RF shielding of the conductors of the implanted lead in accordance with the present invention. FEP and PTFE coatings can be added to the outside diameter (ID) both to enhance slickness (lubrication) to make it easy to insert the lead into the body tissues.

Figure 32:
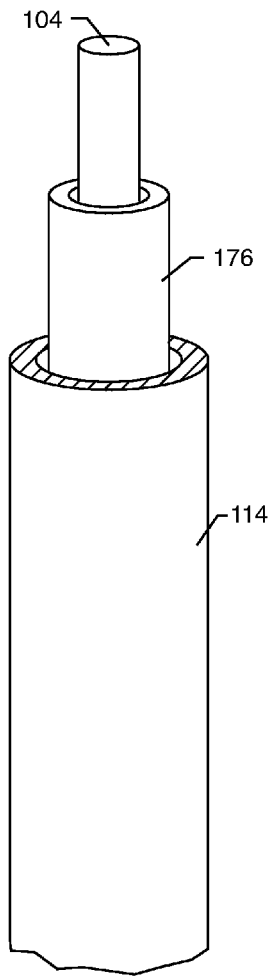
FIG. 32 is similar to FIG. 30, illustrating an alternative embodiment wherein an insulation tube is slipped over the lead, and then an EMI shield is slipped over the insulation tube.

FIG. 32 illustrates an alternative embodiment wherein an insulation tube 176 is slipped over the lead conductor 104. Then, a shield layer 114, such as a platinum-iridium, is slipped over the insulation tube 176 as shown.

Figure 33:
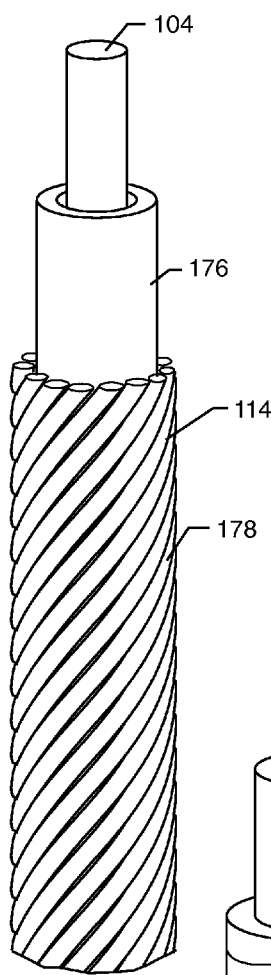
FIG. 33 is similar to FIG. 32, except that the metal EMI shield tube is replaced by wound wire strands.
Figure 34:
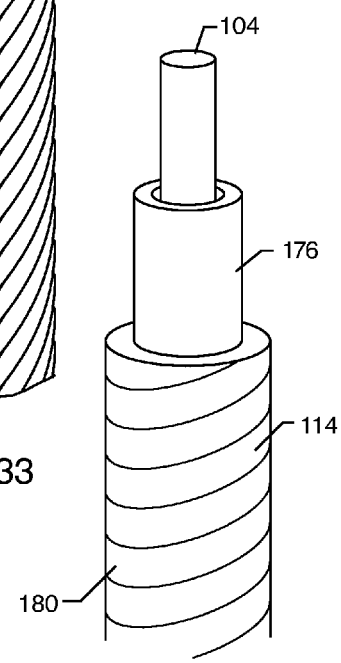
FIG. 34 is similar to FIGS. 32 and 33, except that the EMI shield consists of wrapped foil.

FIGS. 33 and 34 are similar to FIG. 32 except that the metal shield tube 114 is replaced by wound wire strands 178 or wrapped foil 180, respectively, or other equivalent materials which are commonly used in shielded cables worldwide.

Figure 35:
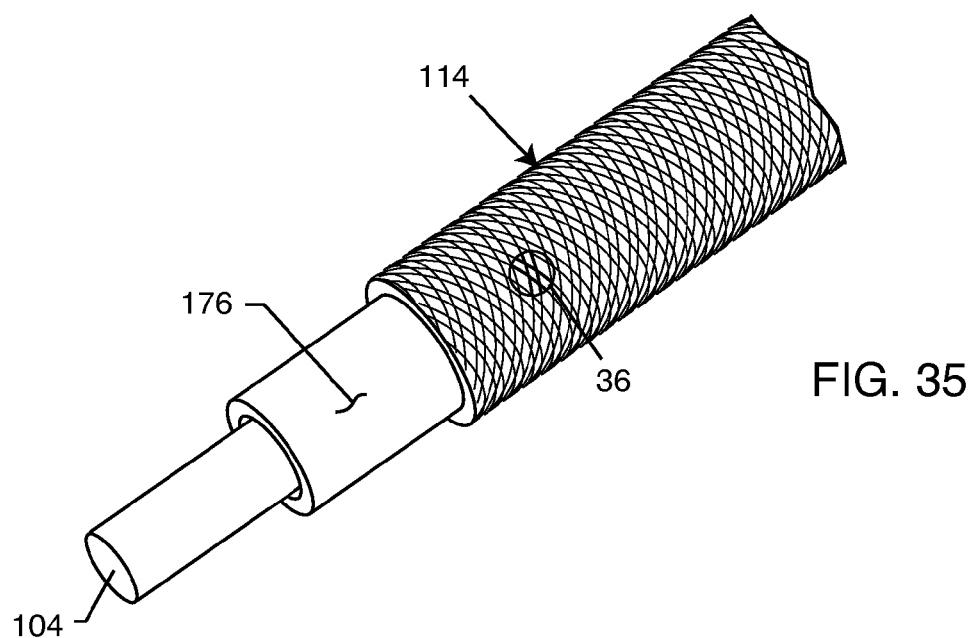
FIG. 35 is similar to FIGS. 32-34, illustrating an EMI shield in the form of an open mesh cross-braided shield wire.
Figure 36:
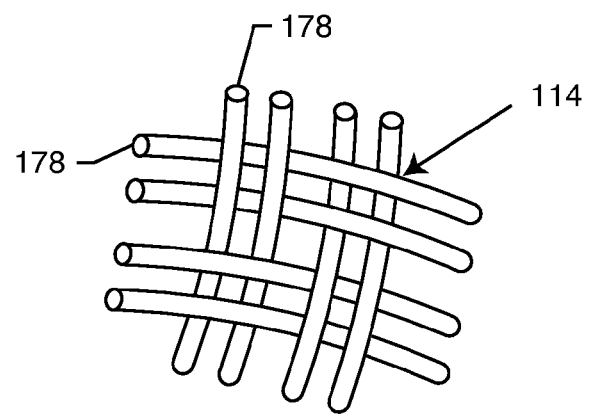
FIG. 36 is an enlarged view taken generally of the area indicated by the number 36 in FIG. 35 illustrating in greater detail the open mesh cross-braided shield wire.

FIG. 35 shows an open mesh cross braided shield wire 114 instead of a wound shield wire (compare to FIG. 33). The cross braid shield 114 is shown in more detail in FIG. 36, wherein one can see how the braided wires 178 interweave.

The thickness of the conductive shield may require precise control. Thin deposition methods are capable of applying films in the nanometer range. The skin depth or effective skin depth, due to limited conductivity from surface scattering and such, of these thin films may be of a thickness that external electromagnetic waves are not fully attenuated.

Most applications will require full or near-full attenuation to prevent significant currents on the internal sensitive components or connections. However it may be desirable that the energy is not fully attenuated, for example when it is desired to limit the amount of current needed to fully attenuate the incident electromagnetic wave to prevent over-heating. Further, multiple shields may be utilized to prevent overheating or allow limited energy to be attenuated on the internal components to allow monitoring of the external environment for applications such as automatic mode switching or data-logging.

From the foregoing, it will be appreciated that the present invention resides in an implantable medical system comprising (1) an active implantable medical device (AIMD), (2) at least one lead having a length exteriorly extending from a proximal end at or adjacent to the AIMD, to a biological sensing or stimulating electrode at a distal end, and (3) an electromagnetic interference (EMI) shield surrounding the at least one lead along at least a portion of the length thereof. The EMI shield may include an electrically conductive exterior surface suitable for long-term exposure to body tissues/fluids. Alternatively or in conjunction therewith, the EMI shield may be conductively coupled to a conductive equipotential surface of the AIMD, which is typically a biocompatible housing for the AIMD.

An insulator may surround the EMI shield along its length. The EMI shield may further comprise a plurality of EMI shields disposed along the length of the at least one lead.

An energy diversion circuit may conductively couple the at least one lead to the EMI shield. Similarly, an impeding circuit may be provided for raising the high frequency impedance of the at least one lead.

Although several embodiments of the invention have been described in detail for the purposes of illustration, various modifications may be made without departing from the spirit and scope of the invention. Accordingly, the invention is not to be limited, except as by the appended claims.

What is claimed is:

1. An implantable medical system, comprising:
   a) an active implantable medical device (AIMD) comprising electronic circuitry hermetically contained inside a device housing, wherein the device housing serves as a conductive equipotential surface;
   b) a hermetic feedthrough terminal supported by the device housing;
   c) at least one lead comprising:
      i) at least one electrical conductor having a length extending from a proximal conductor portion having a proximal conductor end to a distal conductor portion having a distal conductor end, wherein the proximal conductor portion extends through the hermetic feedthrough terminal in a non-conductive relationship with the device housing, and wherein the proximal conductor end is electrically connected to the electronic circuitry housed inside the device housing;
      ii) at least one biological sensing or stimulating electrode, wherein the at least one electrode is electrically connected to the distal conductor portion or the distal conductor end.; and
      iii) at least. one electromagnetic interference (EMI) shield surrounding the at least one electrical conductor in a non-conductive relationship therewith, wherein the EMI shield extends along at least a portion of the conductor length,
   d) wherein a proximal end of the EMI shield by-passes the hermetic feedthrough terminal outside the device housing and is conductively shunted directly to the device housing serving as the conductive equipotential surface.

2. The system of claim 1, including an insulator surrounding either an outside surface of the EMI shield or disposed between the electrical conductor and an inside surface of the shield, or both, wherein the insulator extends along at least a portion of a second length of the EMI shield.

3. The system of claim 1 or 2, wherein the EMI shield comprises a plurality of spaced apart, but electrically connected EMI shields disposed along the length of the at least one electrical conductor.

4. The system of claim 1 or 2, wherein the at least one lead comprises a plurality of leads, and wherein the EMI shield comprises a corresponding plurality of EMI shields.

5. The system of claim 1, wherein the EMI shield comprises a conductive heat-shrink tubing.

6. The system of claim 1, wherein the EMI shield is selected from the group consisting of a conductive foil, a wire, a braid, a mesh, a circuit. trace, a solid tubular material, and a deposited thin film of conductive material.

7. The system of claim 6, wherein the EMI shield is selected from the group consisting of a conductive polymer, a conductive epoxy, and nano-meshes.

8. The system of claim 1, wherein the EMI shield includes one or more stress relief scores.

9. The system of claim 1, wherein the EMI shield is radially spaced from the at least one electrical conductor.

10. The system of claim 1, wherein the EMI shield is of a material selected from the group consisting of MP35N, iridium, platinum, titanium, chromium, Wolfram, tungsten, gold, and copper.

11. The system of claim 1, including a flex cable embodying the at least one electrical conductor and the EMI shield.

12. The system of claim 1 or 2, including an energy diversion circuit conductively coupling the at least one electrical conductor to the EMI shield.

13. The system of claim 12, wherein the energy diversion circuit comprises a low pass filter selected from the group consisting of a capacitor, an inductor, a Pi filter, a T filter, an LL filter, and an "n" element filter.

14. The system of claim 12, wherein the energy diversion circuit comprises at least one series resonant L-C trap filter.

15. The system of claim 1 or 2, including an impeding circuit physically and electrically connected in series with the electrical conductor, wherein the impeding circuit is configured to raise high frequency impedance of the at least one electrical conductor.

16. The system of claim 15, wherein the impeding circuit comprises an inductor.

17. The system of claim 15, wherein the impeding circuit comprises a bandstop filter configured to resonate at or near an MRI RF pulsed frequency.

18. The system of claim 15, including an energy diversion circuit conductively coupling the at least one electrical conductor to the EMI shield.

19. An implantable medical system, comprising:
a) an active implantable medical device (AIMD) comprising electronic circuitry hermetically contained inside a device housing, wherein the device housing serves as a conductive equipotential surface;
b) a hermetic feedthrough terminal supported by the device housing;
c) at least one lead comprising:
  i) at least one electrical conductor having a length extending from a proximal conductor portion having a proximal conductor end to a distal conductor portion having a distal conductor end, wherein the proximal conductor portion extends through the hermetic feedthrough terminal in a non-conductive relationship with the device housing, and wherein the proximal conductor end is electrically connected to the electronic circuitry housed inside the device housing;
  ii) at least one biological sensing or stimulating electrode, wherein the at least one electrode is electrically connected to the distal conductor portion or the distal conductor end; and
  iii) at least one electromagnetic interference (EMT) shield surrounding the at least one electrical conductor in a non-conductive relationship therewith, wherein the EMI shield extends along at least a portion of the conductor length,
d) wherein the EMI shield is an electrically conductive exterior surface suitable for long-term exposure to body tissues and fluids and wherein a proximal end of the EMI shield by-passes the hermetic feedthrough terminal outside the device housing and is conductively shunted directly to the device housing serving as the conductive equipotential surface.

20. The system of claim 19, wherein a non-conductive insulator is disposed between the electrical conductor and the EMI shield, or surrounds the EMI shield, or both.

21. The system. of claim 19, wherein the EMI shield comprises a conductive heat-shrink tubing.

22. The system of claim 19, wherein the EMI shield is selected from the group consisting of a conductive foil, a wire, a braid, a mesh, a circuit trace, and a solid tubular material.

23. The system of claim 19, wherein the EMI shield is selected from the group consisting of a conductive polymer, a conductive epoxy, carbon nano-fibers, nano-meshes, and nano-threads.

24. The system of claim 19, wherein the EMI shield includes one or more stress relief scores.

25. The system of claim 19, wherein the EMI shield is radially spaced from the at least one electrical conductor.

26. The system of claim 19, wherein the EMI shield is selected from the group consisting of MP35N, iridium, platinum, titanium, chromium, Wolfram, tungsten, gold, and copper.

27. The system of claim 19, including a flex cable embodying the at least one electrical conductor and the EMI shield.

28. The system of claim 19, wherein the EMI shield comprises a plurality of spaced apart, but electrically connected EMI shields disposed along the length of the at least one electrical conductor.

29. The system of claim 19, wherein the at least one lead comprises a plurality of leads, and wherein the EMI shield comprises a corresponding plurality of EMI shields.

30. The system of claim 19, including a frequency selective energy diversion circuit conductively coupling the at least one electrical conductor to the EMI shield.

31. The system of claim 30, wherein the energy diversion circuit comprises a low pass filter selected from the group consisting of a capacitor, an inductor, a Pi filter, a T filter, an LL filter, and an "n" element filter.

32. The system of claim 30, wherein the energy diversion circuit comprises at least one series resonant L-C trap filter.

33. The system of claim 19, including an impeding circuit physically and electrically connected in series with the electrical conductor, wherein the impeding circuit is configured to raise the high frequency impedance of the at least one electrical conductor.

34. The system of claim 33, wherein the impeding circuit comprises an inductor.

35. The system of claim 33, wherein the impeding circuit comprises a bandstop filter configured to resonate at or near an MRI RF pulsed frequency.

36. An implantable medical system, comprising:
a) an active implantable medical device (AND) comprising electronic circuitry hermetically contained inside a device housing, wherein the device housing serves as a conductive equipotential surface;
b) a hermetic terminal supported by the device housing;
c) at least one lead comprising:
   i) at least one electrical conductor having a length extending from a proximal conductor portion having a proximal conductor end to a distal conductor portion having a distal conductor end, wherein the proximal conductor portion extends through the hermetic feedthrough terminal in a non-conductive relationship with the device housing, and wherein the proximal conductor end is electrically connected to the electronic circuitry housed inside the device housing;
   ii) at least one biological sensing or stimulating electrode, wherein the at least one electrode is electrically connected to the distal conductor portion or the distal conductor end; and
   iii) at least one electromagnetic interference (EMI) shield comprising a conductive heat-shrink tubing surrounding the at least one electrical conductor in a non-conductive relationship therewith, wherein the EMI shield extends along at least a portion of the conductor length,
d) wherein a proximal end of the EMI shield by-passes the hermetic feedthrouah terminal outside the device housing and is conductively shunted directly to the device housing serving as the conductive equipotential surface.

37. The system of claim 1 or 2, wherein the at least one lead comprises a plurality of lead conductors, and wherein the EMT shield at least partially surrounds the plurality of conductors.

* * * * *

UNITED STATES PATENT AND TRADEMARK OFFICE
CERTIFICATE OF CORRECTION

PATENT NO.        : 8,849,403 B2                             Page 1 of 1
APPLICATION NO.   : 12/788123
DATED             : September 30, 2014
INVENTOR(S)       : Robert Shawn Johnson et al.

It is certified that error appears in the above-identified patent and that said Letters Patent is hereby corrected as shown below:

IN THE CLAIMS

Column 18, line 10 (Claim 19, line 23) delete "EMT" and insert --EMI--

Column 19, line 5 (Claim 36, line 2) delete "AND" and insert --AIMD--

Column 20, line 12 (Claim 36, line 28) delete "feedthrouah" and insert --feedthrough--

Signed and Sealed this
Twelfth Day of January, 2016

Michelle K. Lee
*Director of the United States Patent and Trademark Office*